United States Patent [19]

Yevich et al.

[11] Patent Number: 4,605,655

[45] Date of Patent: Aug. 12, 1986

[54] ANTIPSYCHOTIC 1-FLUOROPHENYLBUTYL-4-(2-PYRIMIDINYL)PIPERAZINE DERIVATIVES

[75] Inventors: Joseph P. Yevich, Newburgh; Walter G. Lobeck, Jr., Evansville, both of Ind.

[73] Assignee: Bristol-Myers Company, New York, N.Y.

[21] Appl. No.: 683,309

[22] Filed: Dec. 18, 1984

Related U.S. Application Data

[63] Continuation-in-part of Ser. No. 586,580, Mar. 6, 1984, abandoned.

[51] Int. Cl.$^4$ ................. A61K 31/505; C07D 403/04; C07D 405/14
[52] U.S. Cl. .................................. 514/252; 544/238; 544/295; 544/319; 544/374
[58] Field of Search ................. 544/295; 424/251; 514/252

[56] References Cited

U.S. PATENT DOCUMENTS

| | | | |
|---|---|---|---|
| 2,973,360 | 2/1961 | Janssen | 544/295 |
| 2,979,508 | 4/1961 | Janssen | 544/295 |
| 2,985,657 | 5/1961 | Janssen | 544/295 |
| 3,299,067 | 1/1967 | Regnier et al. | 544/295 |
| 3,808,210 | 4/1974 | Regnier et al. | 424/251 |
| 4,316,899 | 2/1982 | Markwell | 544/295 |

OTHER PUBLICATIONS

Burger's Medicinal Chemistry, 4th Edition, Part III, M. E. Wolff, Editor, John Wiley & Sons, New York (1981) pp. 917–928.
Chem. Abs., vol. 75, 49136m (1971) (German Offen. DE 2,053,179).
Janssen, "Chemical Abstracts", vol. 55, 1961, col. 5549c.

Primary Examiner—Glennon H. Hollrah
Assistant Examiner—James H. Turnipseed
Attorney, Agent, or Firm—Robert H. Uloth; Richard P. Ryan

[57] ABSTRACT

Disubstituted N,N-piperazinyl derivatives are disclosed wherein one substituent is a pyrimidin-2-yl ring and the other is a 4 carbon chain attached to a p-fluorophenyl ring at the terminal carbon. The terminal carbon of this butylene chain is also bonded to an oxygen atom as part of a carbonyl, carbinol, or ketal functionality. These compounds possess psychotropic properties, particularly atypical antipsychotic activity of good duration. By virtue of pre-clinical pharmacological testing, these compounds appear useful as potential antipsychotic agents which lack the typical movement disorder side-effects of standard antipsychotic agents.

21 Claims, No Drawings

ANTIPSYCHOTIC 1-FLUOROPHENYLBUTYL-4-(2-PYRIMIDINYL)-PIPERAZINE DERIVATIVES

CROSS-REFERENCE TO RELATED APPLICATION

This is a continuation-in-part application of Ser. No. 586,580 filed Mar. 6, 1984 now abandoned.

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein one substituent is pyrimidin-2-yl, preferably substituted by halogen at its 5-position; and the other is a 4 carbon alkylene chain bearing a 4-fluorophenyl ring at its terminus. The terminal carbon is also bonded to an oxygen atom giving either a carbonyl, carbinol, or ketal functional group. Additionally, the terminal carbon can bear a substituent such as an alkyl group or a second 4-fluorophenyl ring.

Related art may be viewed in light of the following general structural formula 1

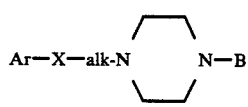
(1)

in which Ar is a phenyl ring, X is a carbonyl or carbinol group, alk is an alkylene chain, and B is a heterocycle. In general, the instant compounds may be classified as relatives of antipsychotic butyrophenone compounds and carbinol derivatives. In this regard, the state of the art is reviewed in Chap. 56 of *Burger's Medicinal Chemistry*, 4th Edition, Part III, M. E. Wolff, Editor, John Wiley & Sons, New York (1981) pages 917–928.

The most closely related art, however, appears to be that contained in a series of three patents issued to Janssen relating to 1-butyl-4-heteroarylpiperazine compounds possessing, among other actions, CNS depressant properties.

In U.S. Pat. No. 2,979,508, issued Apr. 11, 1961, a series of compounds was disclosed in which Ar was substituted phenyl; X was carbonyl or carbinol; alk was $C_1$ to $C_6$ alkylene; and B could be—2-pyrimidinyl or 2-pyridinyl. Compounds (1a) and (1b) were specifically disclosed.

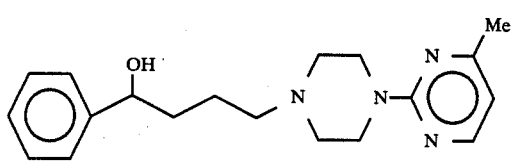
(1a)

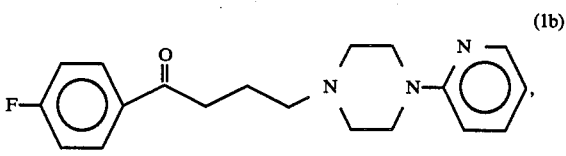
(1b)

also known as Azaperone and used clinically as an antipsychotic agent.

There is no disclosure of a halogen substituent on the pyrimidinyl ring; and no specific disclosure of a fluorophenylbutanol chain coupled to a pyrimidinylpiperazine moiety.

In U.S. Pat. No. 2,985,657, issued May 23, 1961; a series of butyrophenones was disclosed in which Ar was halophenyl; X was carbonyl, alk was $C_1$ to $C_4$ alkylene; and B was pyrimidinyl and chloropyridazinyl among other heterocycles. Specifically disclosed were the following two compounds shown below as (1c) and (1d).

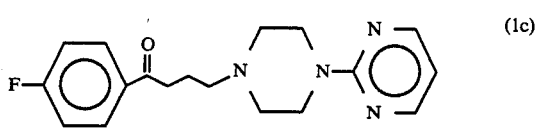
(1c)

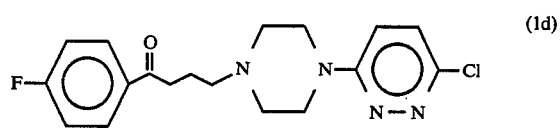
(1d)

Compound (1c) has also been disclosed in German Offen. DE No. 2,053,759, May 27, 1971. Again, no halogenated pyrimidinyl rings were disclosed or claimed.

In U.S. Pat. No. 2,973,360, issued Feb. 28, 1961; a series of CNS depressant compounds is disclosed with Ar being 2-thienyl; X being carbonyl or carbinol; alk being $C_2$ and $C_3$ alkylene; and B being 2-pyrimidinyl or 2-pyridyl. The most pertinent compound specifically exemplified and claimed in this patent is shown below as structure (1e).

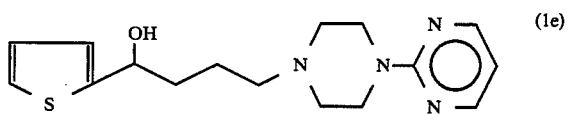
(1e)

The following references, while related, are less relevant to the new compounds disclosed in this application.

Regnier, et al., U.S. Pat. No. 3,299,067, issued Jan. 17, 1967 discloses compounds comprising a benzyl-type moiety attached to the 2-pyrimidinylpiperazine. A specific example of this series which is said to be useful as peripheral vasodilators, analgesics and antiinflammatory agents, is shown below as structure (2).

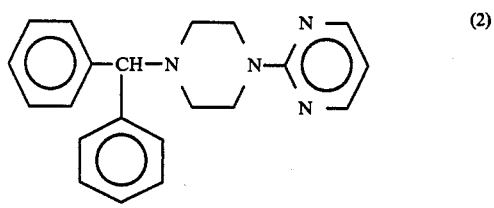
(2)

U.S. Pat. No. 3,808,210, issued to Regnier, et al., in April 1974 relates to a series of aryloxypropanolamine antihypertensive compounds having a pyrimidinylpiperazine moiety as in (3). However, these compounds are not butyrophenones or derivatives.

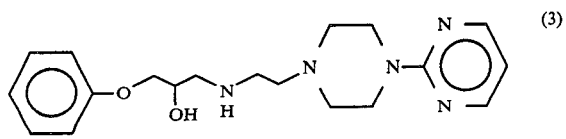

U.S. Pat. No. 4,316,899 issued to Markwell on Feb. 23, 1982 relates to another series of aryloxypropanolamine antihypertensive compounds containing a pyrimidinylpiperazine moiety as exemplified by structure (4).

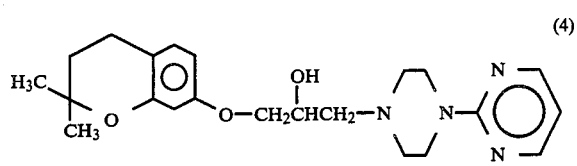

SUMMARY AND DETAILED DESCRIPTION OF THE INVENTION

In its broadest aspect, the present invention is concerned with piperazinyl butyrophenone derivatives having neuroleptic (antipsychotic) properties characterized by a compound of Formula I

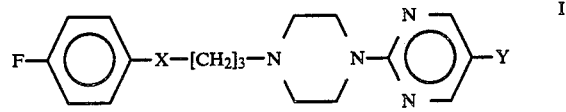

wherein X is

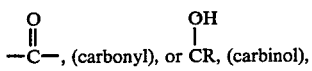

with R being $C_{1-4}$ alkyl, hydrogen or fluorophenyl; and Y is hydrogen or halgen with the proviso that when X is the carbonyl moiety, Y is only halogen; or a pharmaceutically acceptable acid addition salt thereof.

It is to be understood that, as used herein, halogen denotes chlorine, bromine, iodine and preferably fluorine. Preferred compounds are those wherein X is carbinol with R=H and wherein Y is fluorine. In the most preferred compound X is

and Y is fluorine.

It is also to be understood that the present invention is considered to include stereoisomers as well as optical isomers, e.g. mixtures of enantiomers as well as individual enantiomers and diastereomers, which arise as a consequence of structural asymetry in the carbinol compounds of the instant series. Separation of the individual isomers is accomplished by application of various methods which are well known to practitioners in the art.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of structure I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid, and the like; useful inorganic acids are hydrohalide acids such as HCl, HBr, HI; sulfuric acid; phosphoric acid; and the like.

The compounds of the instant invention are useful pharmacological agents with psychotropic properties. In this regard, they exhibit selective central nervous system activity at non-toxic doses and are of particular interest as neuroleptic (antipsychotic) agents. As with other known antipsychotics, the compounds of Formula I evoke certain responses when studied in standard in vivo and in vitro pharmacological test systems which are known to correlate well with relief of symptoms of acute and chronic psychosis in man. The following in vivo test systems are illustrative of the conventional testing used to classify and differentiate a psychotropic agent from a non-specific CNS depressant and determine potential side-effect liabilities such as cataleptic activity.

TABLE 1
In Vivo Tests Used to Evaluate Formula I Compounds

1. *Conditioned Avoidance Response (CAR)*—measure of a drug's tranquilizing activity as determined by its attenuation of avoidance response to electrical shock in trained fasted rats. cf: Albert, *Pharmacologist*, 4, 152 (1962); Wu, et al, J. Med. Chem., 12, 876–881 (1969).
2. *Inhibition of Apomorphine-Induced (APO) Stereotype*—an assessment of blockade of dopaminergic activity in rats as measured by attentuation of the behavioral syndrome caused by the dopamine agonist, apomorphine. cf. Janssen, et al, *Arzneimittel. Forsch.*, 17, 841 (1966).
3. *catalepsy*—drug-induced catalepsy in rats is predictive of potential extrapyramidal symptoms (EPS) in man. cf: Costall, et al, *Psychopharmacologia*, 34, 233–241 (1974); Berkson, J. *Amer. Statist. Assoc.*, 48, 565–599 (1953).
4. *Catalepsy Reversal*—measure of a drug's ability to reverse neuroleptic-induced catalepsy in the rat.
5. *Inhibition of Norepinephrine Lethality*—drug inhibition of the lethality of noradrenergic drug norepinephrine indicates $\alpha_1$-adrenergic blockade.
6. *Sidman Avoidance Test*—predicts antipsychotic activity when animal's avoidance behavior is disrupted without affecting its escape behavior. cf: Hill and Tedeschi, "An Introduction to Psychopharmacology", Reck and Moore (Eds.), Raven Press, New York, 1971, page 276.

Butyrophenones, such as haloperidol, and most derivatives which are effective in the treatment of schizophrenia are also potent dopaminergic antagonists. However, therapeutic utility of these agents is compromised by serious side effects, particularly movement disorders. The short-term use of butyrophenones often results in Parkinsonism-like extrapyramidal side effects (EPS) while their chronic administration may cause the severe and often irreversable syndrome of tardive dyskinesia. While in general the compounds of Formula I of this invention exhibit significant antipsychotic activity at dose levels far below those which may induce catalepsy, certain representative members of this series also demonstrate catalepsy-attenuating effects which would strengthen a prediction that these compounds would be void of EPS liability.

As further indication of the psychotropic activity and specificity of the instant compounds, state of the art in vitro central nervous system receptor binding methodology can be employed. Certain compounds (commonly referred to as ligands) have been identified which preferentially bind to specific high affinity sites in brain tissue dealing with psychotropic activity or potential for side effects. Inhibition of radiolabeled ligand binding to such specific high affinity sites is considered a measure of the compound's ability to affect corresponding central nervous system function or cause side effects in vivo. This principal is employed in the following assays which are given by way of example.

TABLE 2

In Vitro Radioreceptor Binding Assays for Evaluation of Formula I Compounds

| Receptor Binding Assay | Reference |
|---|---|
| Dopamine | Burt, et al., Molec. Pharmacol., 12, 800 (1976); Science, 196, 326 (1977); Creese, et al, Science, 192, 481 (1976). |
| Cholinergic | Yamamura, et al., Proc. Natn. Acad. Sci. USA 71, 1725 (1974). |
| Alpha-receptor | Crews, et al., Science, 202: 322 (1978); Rosenblatt, et al., Brain Res., 160: 186 (1979); U'Prichard, et al., Science, 199: 197 (1978); U'Prichard, et al., Molec. Pharmacol., 13: 454 (1977). |
| Serotonin Type 2 | Peroutka and Snyder, Molec. Pharmacol., 16: 687 (1979). |

According to the pharmacological profile established by all these aforementioned tests, the instant compounds of Formula I have promising antipsychotic potential in that they are relatively potent in the standard Conditioned Avoidance Response test, Sidman avoidance test, and Inhibition of Apomorphine Stereotypy test, having oral $ED_{50}$ values $\leq 100$ mg/kg body weight in these three tests. Activity in these tests is considered predictive of antipsychotic potential in man. Concerning side effect liability, the instant compounds are inactive in catalepsy production or alpha-block by virtue of oral $ED_{50}$ values being $>100$ mg/kg. Even more significantly, preferred compounds of the invention demonstrate the ability to reverse catalepsy with $ED_{50}$ values of $<20$ mg/kg, given orally. Surprisingly, preferred compounds of the instant invention demonstrate very low activity in the inhibition of [$^3$H]spiperone binding by virtue of having $IC_{50}$ values $>1000$ nM. This lack is potency in dopaminergic binding of these compounds in striatal tissue coupled with significant potency in the conditioned avoidance testing and inhibition of apomorphine stereotypy suggest that the instant compounds are atypical antipsychotic agents.

The most preferred compound of the instant invention (X=—CHOH— and Y=F; also known as MJ 14802) is essentially inactive at serotonergic, $\alpha_2$-adrenergic, cholinergic, GABA and opiate binding sites. The duration of action of MJ 14802 in the inhibition of the CAR and apomorphine stereotypy was found to be $>7$ and 4 hours, respectively. In contrast, the CAR activity of the des-fluoro analog of MJ 14802 (Y=H) is lost after three hours.

Table 3 shows a comparison of the biological profiles of MJ 14802 with those of the standard reference drugs thioridazine and clozapine. On the basis of conditioned avoidance response and inhibition of apomorphine stereotypy testing data, it is expected that the instant compounds would be used as antipsychotic agents in the same manner as the reference agent clozapine.

TABLE 3

Comparison of Biological Data for Thioridazine, Clozapine, and MJ 14802

| Test | Thioridazine | Clozapine | MJ 14802 |
|---|---|---|---|
| CAR $ED_{50}$, mg/kg, p.o. | 126.0 | 24.0 | 26.4 |
| Inhibition of APO-Stereotypy $ED_{50}$, mg/kg, p.o. | 280.0 | 49.2 | 33.0 |
| Inhibition of NE Lethality $ED_{50}$, mg/kg, p.o. | 2.2 | 3.5 | >100 |
| Catalepsy $ED_{50}$, mg/kg, p.o. | 45.2 | >200 | >100 |
| Catalepsy Reversal $ED_{50}$, mg/kg, p.o. | I | I | 16.9 |
| DA Binding (vs. [$^3$H]spip.) $IC_{50}$, nM | 67 | 569 | 6400 |
| $\alpha_1$ Binding (vs. [$^3$H]WB4101) $IC_{50}$, nM | 65 | 62 | 520 |
| Muscarinic Cholinergic Binding $IC_{50}$, nM | 106 | 91 | >1000 |

I = Inactive

As can be seen MJ 14802 appears to be a potential atypical antipsychotic. In this regard, it exhibits potency and duration of action in in vivo tests which are predictive of antipsychotic efficacy. Unique aspects of this compound include its very weak dopamine receptor binding and the fact that it not only fails to cause catalepsy but also reverses neuroleptic-induced catalepsy. Additionally, MJ 14802 lacks anticholinergic and $\alpha_1$-adrenergic activities; one or both of these activities contribute to the side effects of virtually all marketed and experimental antipsychotic drugs.

In summary of the foregoing discussion, the instant compounds have psychotropic properties particularly suited to their use as a neuroleptic (antipsychotic) agent. Thus, another aspect of the instant invention concerns a process for ameliorating a psychotic state in mammal in need of such treatment which comprises systemic administration to such mammal of an effective dose of a Formula I compound or a pharmaceutically acceptable acid addition salt thereof. The administration and dosage regimen of compounds of Formula I is considered to be done in the same manner as for the reference compound clozapine, cf: The Merck Index, 10th Edition, (1983), page 344, and references therein. On the basis of animal testing an effective oral dose could be expected to be from about 2 to 50 mg/kg and an effective parenteral dose could be expected to be lower, in the range of about 0.05 to 1 mg/kg body weight.

Although the dosage and dosage regimen must in each case be carefully adjusted, utilizing sound professional judgement and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably 2 to 30 mg/kg, when administered orally. In some instances, a sufficient therapeutic effect can be obtained at lower doses while in others, larger doses will be required.

The term systemic administration as used herein refers to oral, rectal, and parenteral (i.e., intramuscular, intravenous, and subcutaneous) routes. Generally, it will be found that when a compound of the present invention is administered orally which is the preferred route, a larger quantity of the active agent is required to produce the same effect as the smaller quantity given parenterally. In accordance with good clinical practice, it is preferred to administer the instant compounds at a concentration level that will produce effective neuroleptic (antipsychotic) effects without causing any harmful or untoward side effects.

Therapeutically, the instant compounds are generally given as pharmaceutical compositions comprised of an effective antipsychotic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with a pharmaceutical carrier, the carrier comprising one or more solid, semi-solid, or liquid diluent, filler and formulation adjuvant which is non-toxic, inert and pharmaceutically acceptable. Such pharmaceutical compositions are preferably in dosage unit forms; i.e., physically discrete units containing a pre-determined amount of the drug corresponding to a fraction or multiple of the dose which is calculated to produce the desired therapeutic response. The dosage units can contain 1, 2, 3, 4, or more single doses, or, alternatively, ½, ⅓, or ¼ of a single dose. A single dose preferably contains an amount sufficient to produce the desired therapeutic effect upon administration at one application of one or more dosage units according to the pre-determined dosage regimen, usually a whole, half, third or quarter of the daily dosage administered once, twice, three or four times a day. Other therapeutic agents can also be present. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propylene glycol, and polyethyleneglycols or mixtures thereof. The polyethyleneglycols consist of a mixture of non-volatile, usually liquid, polyethyleneglycols which are soluble in both water and organic liquids and which have molecular weights of from about 200 to 1500.

The general procedures for the preparation of compounds of Formula I are outlined in Scheme 1

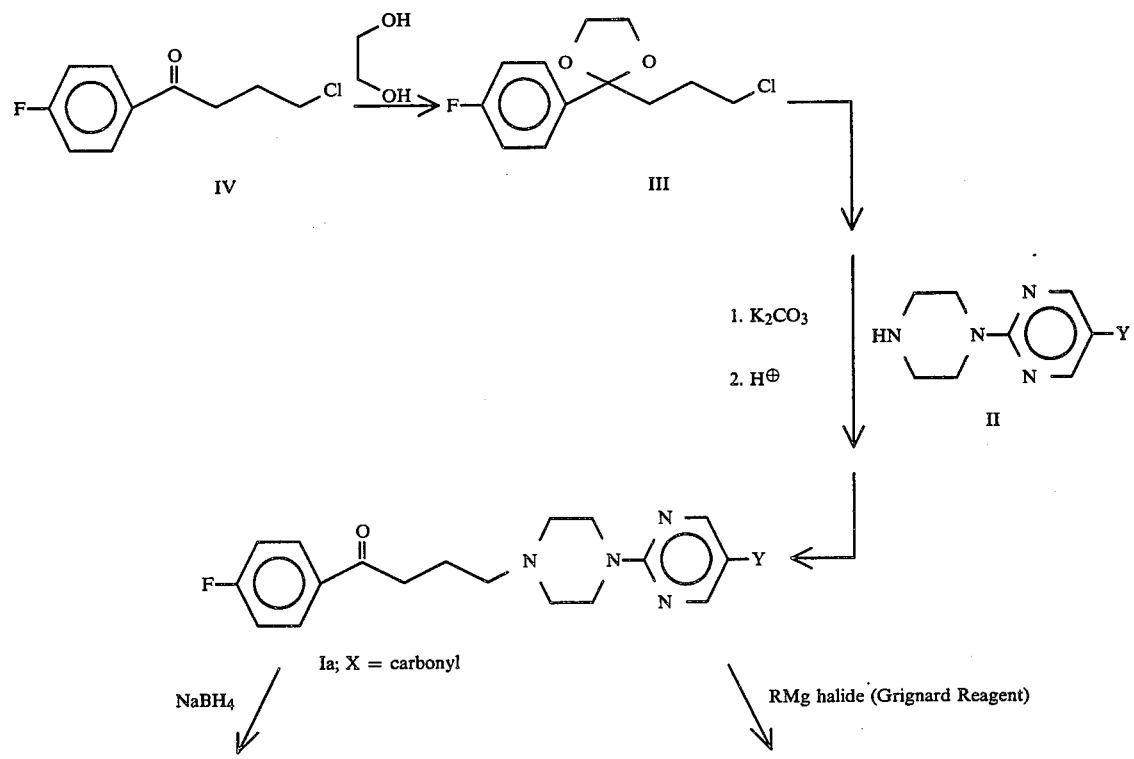

Scheme 1

-continued
Scheme 1

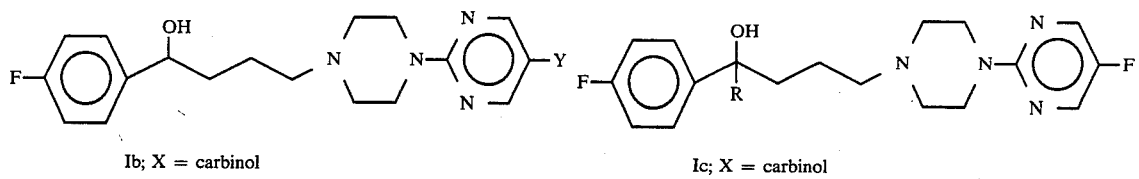

Ib; X = carbinol

Ic; X = carbinol

As shown in Scheme 1 a 5-Y substituted 1-pyrimidin-2-ylpiperazine (II) is alkylated with the γ-chloro ketal (III; prepared from the commercially available ketone IV) in the presence of $K_2CO_3$ to afford, following acidic work up, the ketone product, Ia; X=carbonyl. Treatment of Ia with $NaBH_4$ in ethanol produces the secondary carbinols Ib; X=carbinol in 50–70% yield. Reaction of Ia with Grignard reagents affords the tertiary carbinols Ic. In the above scheme R and Y are as described hereinabove.

The procedure for preparing compounds of structure Ia involves reaction conditions commonly employed in preparing tertiary amines by alkylating secondary amines. Thus, the compounds of Ia are obtained by reacting appropriate intermediates, II and III, in an inert reaction medium at temperatures of from about 50° to about 200° C. in the presence of a base suitable for use as an acid binding agent. Operable inorganic and organic acid binding bases include tertiary amines, alkali and alkaline earth metal carbonates, bicarbonates, or hydrides with sodium carbonate and potassium carbonate particularly preferred. As referred to throughout the specification, the term "inert reaction medium" refers to any protic or aprotic solvent or diluent which does not enter into the reaction to any substantial degree. In this regard, acetonitrile is particularly preferred solvent with the reaction conveniently carried out at the reflux temperature. Satisfactory yields of the present compounds are obtained with reaction periods ranging from about 2 to 24 hours. Formula Ia products may be purified by crystallization techniques from standard solvent media such as acetonitrile, isopropanol, methanol, ethanol, and the like and by other conventional methods such as chromatography employing a silica gel column which mixtures of chloroform and alkanols such as methanol and ethanol as eluent. It is obvious to a practitioner skilled in the chemical arts that the intermediate III has a ketal functionality at the carbon atom joined to the para-fluorophenyl residue. The ketal functionality serves, in this instance, as a protecting group for the incipient carbonyl moiety. Following the alkylation step, mild treatment with dilute acid, HCl preferred, smoothly breaks down the ketal protecting group to afford the desired carbonyl functionality.

Reduction of Ia is achieved using an alcoholic slurry of sodium borohydride with ethanol preferred as the alkanol reaction liquid to give to secondary carbinol product Ib. A tertiary carbinol product, Ic, is conveniently prepared from the carbonyl compound Ia by reaction with an appropriate Grignard reagent prepared in the usual manner from an alkyl or aryl halide and magnesium turnings in dry ether, tetrahydrofuran being preferred. Alternatively, the same chemical conversion can be achieved using other appropriate organometallic reagents. Additional methods and modifications of these methods would be apparent to one skilled in the chemical arts.

The 5-halogenated pyrmidinylpiperazine intermediates may be prepared by several procedures as shown in Scheme 2.

Scheme 2

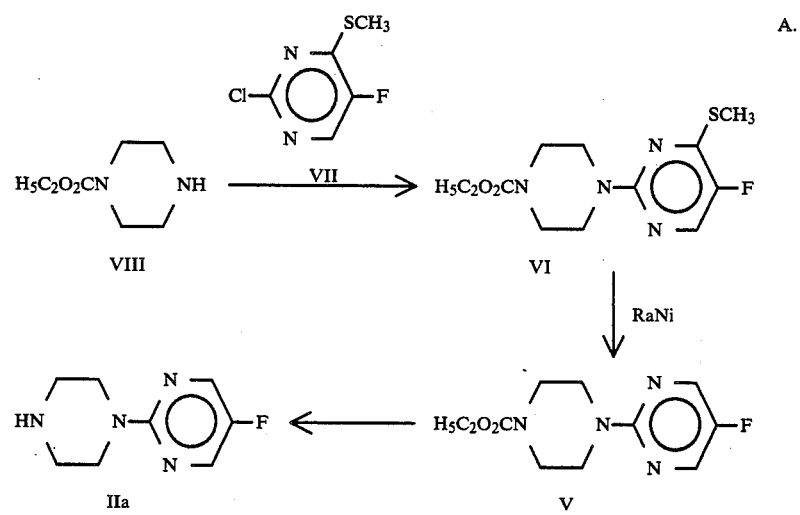

Scheme 2

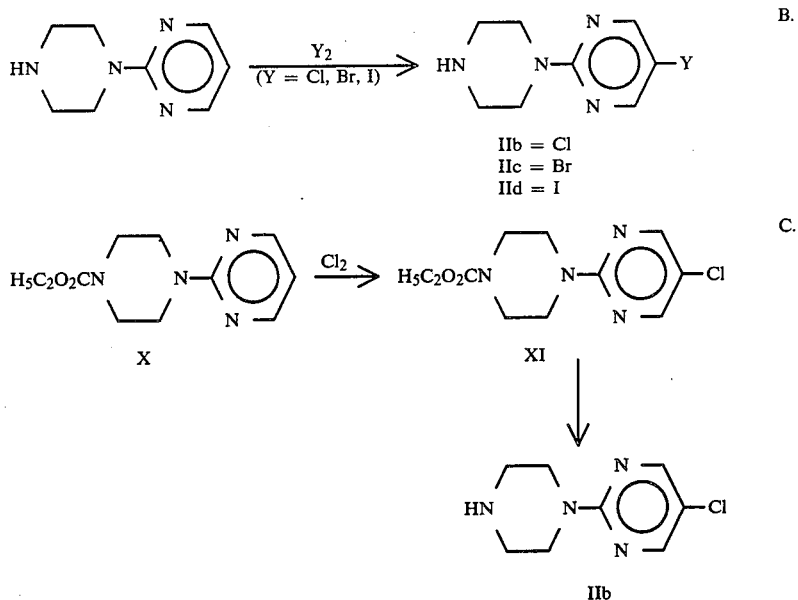

The 5-fluoro derivative (IIa) is obtained from the intermediate compound 2-chloro-5-fluoro-4-methylthiopyrimidine (VII) by treatment with N-carbethoxypiperazine (VIII), followed by Raney Nickel desulfurization to give V and acid-catalyzed removal of the carbethoxy group giving IIa. The intermediates II where Y is chloro, bromo, or iodo may be obtained by direct halogenation of 1-pyrimidin-2-ylpiperazine itself, as in procedure B, although in the case of Y=chloro, better yields are realized by chlorination of N-carbethoxy-1-pyrimidin-2-ylpiperazine (X) and subsequent cleavage of the carbethoxy group of XI to give the desired 5-chloro-pyrimidinylpiperazine, IIb.

Certain of the intermediate compounds used in the synthetic procedures discussed hereinabove are available commercially, e.g. compounds IV, VIII, IX and therefore no examples nor description of their preparation need be given.

DESCRIPTION OF SPECIFIC EMBODIMENTS

The compounds which constitute this invention and their methods of preparation will appear more full from a consideration of the following examples which are given for the purpose of illustration only and are not to be construed as limiting the invention in sphere or scope. All temperatures are understood to be in degrees C. when not specified.

The nuclear magnetic resonance (NMR) spectral characteristics refer to chemical shifts (δ) expressed as parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), or quartet (q). Abbreviations employed are DMSO-$d_6$ (deuterodimethylsulfoxide), $CDCl_3$ (deuterochloroform), and are otherwise conventional. The infrared (IR) spectral descriptions include only absorption wave numbers ($cm^{-1}$) having functional group identification value. The IR determinations were employed using potassium bromide (KBr) as diluent. The elemental analyses are reported as percent by weight.

SYNTHESIS OF INTERMEDIATES

EXAMPLE 1

γ-Chloro-p-fluorobutyrophenone Ethylene Ketal (III)

A solution of γ-chloro-p-fluorobutyrophenone (50 g, 0.25 mole, commercially available); ethylene glycol (50 mL); p-toluene sulfonic acid (0.1 g) in 300 mL benzene is refluxed for 18 hrs with water of reaction being removed by means of a Dean Stark water trap. Upon cooling to room temperature, the reaction mixture is washed with dilute sodium bicarbonate, dried ($MgSO_4$), filtered and the benzene removed by concentration in vacuo. The residual oil was distilled to give 57.7 g (93%) of product, b.p. 106-112/0.01 Torr.

EXAMPLE 2

5-Fluoro-2-(1-piperazinyl)pyrimidine (IIa)

(1) Ethyl-4-(5-fluoro-4-methylthio-2-pyrimidinyl)-1-piperazine carboxylate (VI): A mixture of 2-chloro-5-fluoro-4-methylthiopyrimidine (VII, 28.3 g, 0.16 mole), N-carbethoxypiperazine (VIII, 25.26 g, 0.16 mole), anhydrous $K_2CO_3$ (66.0 g) and a catalytic amount of KI in acetonitrile (400 mL) was stirred and heated under reflux for 18 hrs. The hot reaction mixture was filtered, concentrated in vacuo and the residue crystallized from ethanol to give 29.8 g (62%) of product.

(2) Ethyl-4-(5-fluoro-2-pyrmidinyl)-1-piperazine carboxylate (V): A mixture of ethyl-4-(5-fluoro-4-methylthio-2-pyrimidinyl)-1-piperazine carboxylate (VI, 29.8 g, 0.1 mole) and Raney Nickel catalyst (15 tsp) in ethanol (550 mL) was stirred and heated under reflux for 48 hrs. The reaction mixture was filtered, concentrated in vacuo and the residue recrystallized twice from ethanol to provide 11.2 g (45%) of product, m.p. 104°-107°.

A solution of this intermediate (V, 11.2 g, 0.04 mole) in 6N HCl (100 mL) was stirred and heated under reflux overnight. The cooled reaction mixture was made alkaline by addition of 50% NaOH, extracted with ether and the extract dried (MgSO$_4$) and concentrated in vacuo to provide 7.23 g (100%) of product as a viscous oil which can be treated with ethanolic HCl in ethanol to yield the hydrochloride salt, m.p. 250°–252°.

Anal. Calcd. for C$_8$H$_{11}$FN$_4$.HCl: C, 43.95; H, 5.54; N, 25.63. Found: C, 44.23; H, 5.57; N, 25.38.

The above examples serves to illustrate the procedure A in Scheme 2.

EXAMPLE 3

5-Bromo-2-(1-piperazinyl)pyrimidine (IIc)

This example serves to illustrate procedure B of Scheme 2. To an ice-cooled solution of 1-(2-pyrimidinyl)piperazine (16.4 g, 0.1 mole) in 1N HCl (100 mL) was added dropwise bromine (15.98 g, 0.1 mole). After stirring at 0° for 0.5 hr, the mixture was heated to 100° until dissipation of the red color had occurred. The mixture is filtered, cooled, made alkaline with 50% NaOH and extracted with ether. The dried extract (MgSO$_4$) was concentrated in vacuo to provide 14.5 g (62%) of product, m.p. 73°–75°.

By appropriate modification of this procedure, the 5-chloro intermediate, IIb, and the 5-iodo intermediate, IId, may be prepared.

EXAMPLE 4

5-Chloro-2-(1-piperazinyl)pyrimidine (IIb)

This example illustrates procedure C of Scheme 2. Chlorine gas was bubbled into a solution of ethyl-4-(2-pyrimidinyl)-1-piperazine carboxylate (31.4 g, 0.133 mole) in 1N HCl (150 mL) for 15 minutes. The reaction mixture was cooled in ice and the solid product collected by filtration and dried to afford 19.3 g (54%) of the 5-chloro-N-carbethoxy intermediate compound, m.p. 80°–83°. This intermediate was hydrolyzed under acidic conditions as described for the 5-fluoro analog in Example 2. From 19.3 g (0.07 mole) of the N-carbethoxy intermediate compound was obtained 10.7 g (77%) of IIb.

EXAMPLE 5

5-Iodo-2-(1-piperazinyl)pyrimidine (IId)

Preparation of this reaction intermediate may be achieved by modification of preparations given for synthesis of some 2-amino-5-iodopyrimidines as described in J. P. English, et al., JACS, 68, 1039 (1946).

A refluxing mixture of 1-(2-pyrimidinyl)piperazine (5.0 g, 0.03 mole) and mercuric acetate (19.2 g, 0.06 mole) in 90 mL glacial acetic acid is treated with iodine (9.4 g, 0.037 mole). After 15 minutes, the reaction mixture is then added to a solution of potassium iodide (21 g) and sodium sulfite (4.5 g) in 125 mL water. The resulting mixture is filtered and the filtrate neutralized with 50% NaOH solution and extracted with methylene chloride. The methylene chloride extract is washed successively with potassium iodide solution and sodium sulfite solution, dried (MgSO$_4$) and concentrated in vacuo the desired product.

SYNTHESIS OF I PRODUCTS

EXAMPLE 6

1-(4-Fluorophenyl)-4-[4-(5-fluoro-2-pyrimidinyl)-1-piperazinyl]butanone Hydrochloride (Ia)

A mixture of 5-fluoro-2-(1-piperazinyl)pyrimdine (IIa, 7.3 g, 0.04 mole), γ-chloro-p-fluorobutyrophenone ethylene ketal (IV, 14.5 g, 0.06 mole), anhydrous K$_2$CO$_3$ (24.8 g) and a catalytic amount of KI in acetonitrile (100 mL) was stirred and heated under reflux for 36 hrs. The hot mixture was filtered, concentrated in vacuo and the residue treated with 20 mL of 3N HCl and 100 mL ethanol. After cooling in ice, the product was collected by filtration and dried to give 7.6 g (50%) of product as a white solid, m.p. 234°–236°.

Anal. Calcd. for C$_{18}$H$_{20}$F$_2$N$_4$O.HCl: C, 56.48; H, 5.53; N, 14.64. Found: C, 56.27; H, 5.52; H, 14.27.

NMR (DMSO-d$_6$): 2.10 (2,m); 3.20 (6,m); 3.54 (4,m); 4.58 (2,m); 7.34 (2,m); 8.08 (2.m); 8.55 (2,s); 11.60 (1,bs).

IR (KBr): 960, 1235, 1245, 1365, 1510, 1560, 1600, 1680, 2550, and 2920 cm$^{-1}$.

EXAMPLE 7

4-[4-[5-Fluoro-2-pyrimidinyl]-1-piperazinyl]-1-(4-fluorophenyl)butanol Hydrochloride (Ib, MJ 14802-1)

A mixture of the Ia compound prepared above in Example 6 (7.6 g, 0.02 mole) and sodium borohydride (2.3 g, 0.06 mole) in ethanol (650 mL) was stirred overnight. The mixture was treated with ethanolic HCl, stirred at room temperature for 1.5 hr, then heated to reflux. Solvent was removed in vacuo and to the residue was added 1N NaOH and methylene chloride. The organic layer was separated, dried (MgSO$_4$) and concentrated in vacuo. This residue was dissolved in ethanol (treated with ethanolic HCl and cooled). The hydrochloride salt was collected by filtration and dried to afford 6.2 g (81%) of product, m.p. 236°–238°.

Anal. Calcd. for C$_{18}$H$_{22}$F$_2$N$_4$O.HCl: C, 56.18; H, 6.03; N, 14.56. Found: C, 55.98; H, 6.06; N, 14.23.

NMR (DMSO-d$_6$): 1.71 (2,m); 3.10 (4,m); 3.47 (4,m); 4.59 (3,m); 5.30 (1,bs); 7.11 (2,m); 7.40 (2,m); 8.53 (2,s); 11.50 (1,bs).

IR (KBr), 955, 1220, 1235, 1370, 1440, 1455, 1480, 1510, 1560, 1605, 2600, and 2920 cm$^{-1}$.

EXAMPLE 8

α,α-bis-(4-fluorophenyl)-4-(5-fluoro-2-pyrimidinyl)-1-piperazinebutanol Hydrochloride (Ic)

To the Grignard reagent prepared in the usual manner from 4-bromofluorobenzene (6.3 g, 0.03 mole) and magnesium turnings (0.73 g, 0.03 mole) in dried tetrahydrofuran (40 mL) was added a solution of the Ia compound prepared above in Example 5 (7.87 g, 0.023 mole) in tetrahydrofuran (40 mL). The mixture was stirred and heated under reflux for 18 hr, cooled and treated with NaCl solution. The decanted tetrahydrofuran solution was concentrated in vacuo to remove solvent and the oily residue was flash-chromatographed on silica gel using hexane-ethyl acetate, 3:7, as eluent. Fractions containing a single component (Rf 0.43 in hexane-ethyl acetate, 3:7) were combined and concentrated in vacuo to provide 5.2 g of a viscous oil. An ethanol solution of the latter was treated with ethanolic HCl following which the ethanol was removed in vacuo and the residue was azeotroped in 100 mL benzene. Concentration of this resulting solution at atmospheric pressure to half volume resulted in separation of a solid. The solid product was collected by filtration and dried to afford 1.9 g (17%) of the tertiary carbinol product, m.p. 153°-155°.

Anal. Calcd. for $C_{24}H_{25}F_3N_4O \cdot HCl$: C, 60.19; H, 5.47; N, 11.70. Found: C, 60.30; H, 5.36; N, 11.78.

NMR (DMSO-$d_6$): 1.66 (2,m); 2.34 (2,m); 3.08 (4,m); 3.42 (4,m); 4.50 (2,m); 5.82 (1,bs); 7.07 (4,m); 7.46 (4,m); 8.50 (2,s); 11.30 (1,bs).

IR (KBr): 835, 950, 1220, 1235, 1365, 1450, 1490, 1510, 1560, 1605, 2590, and 2930 cm$^{-1}$.

Using the appropriate starting compounds, additional examples of Formula I products may be synthesized using substantially the same procedures as outlined hereinabove. Some additional products of Formula I which may be synthesized are shown in Table 4. Formula I compounds in which

are prepared using the procedure given in Example 6. Formula I compounds wherein X=CHOH may be prepared using the procedure given in Example 7, and those wherein X=CROH may be prepared according to Example 8.

TABLE 4
Additional Formula I Products

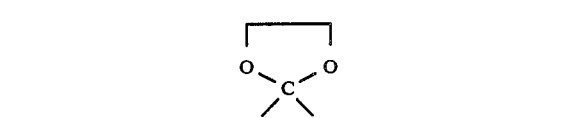

| Example | X | Y | m.p. °C. | Yield %[a] | Formula[b] |
|---|---|---|---|---|---|
| 9 | C=O | Cl | 115–117 | 45 | $C_{18}H_{20}ClFN_4O$ |
| 10 | C=O | Br | 129–131 | 33 | $C_{18}H_{20}BrFN_4O$ |
| 11 | C=O | I | — | — | $C_{18}H_{20}FIN_4O$ |
| 12 | CHOH | H | 204–206 | 56 | $C_{18}H_{23}FN_4O \cdot HCl$ |
| 13 | CHOH | Cl | 230–232 | 50 | $C_{18}H_{22}ClFN_4O \cdot H_2O$ |
| 14 | CHOH | Br | 235–237 | 54 | $C_{18}H_{22}BrFN_4O \cdot HCl$ |
| 15 | CHOH | I | — | — | $C_{18}H_{22}FIN_4O$ |
| 16 | $C_2H_5$COH | F | 208–210 | 24 | $C_{20}H_{21}F_2N_4O \cdot HCl$ |
| 17 | p-F—$C_6H_4$COH | H | 219–221 | 42 | $C_{24}H_{26}F_2N_4O \cdot HCl$ |
| 18 | $CH_3$COH | F | 192–194 | 25 | $C_{19}H_{24}F_2N_4O \cdot HCl$ |

[a] All compounds were recrystallized from ethanol.
[b] C, H, and N analyses were all within ±0.4% of calculated values for compounds with melting points.

FURTHER DETAILED DESCRIPTION OF THE INVENTION

Some additional compounds similar to those defined hereinbefore by Formula I also have antipsychotic properties. For instance, they are active in the Conditioned Avoidance Response test at non-catalepsy producing doses of below 100 mg/kg and also demonstrate very little activity in the inhibition of [$^3$H]spiperone binding by virtue of having IC$_{50}$ values >1000 nM. The significance of these findings as they relate to antipsychotic potential has already been adequately discussed for Formula I compounds. Formula XXI (shown below) expands the scope of the invention to include all of these additional substances, as illustrated in Examples 19 and 20 and having the structure given here as Formula I'. This additional subject matter comprises compounds of Formula I'

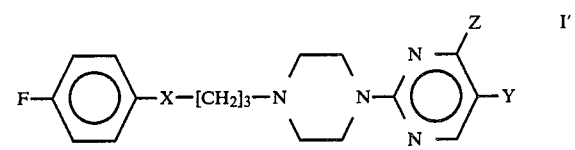

or a pharmaceutically acceptable acid addition salts and/or solvate thereof wherein x is

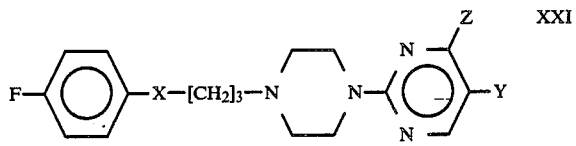

or —CHOH—; Y is halogen or hydrogen; and Z is alkyl or hydrogen. Thus, the present redefined invention comprehends a compound of Formula XXI

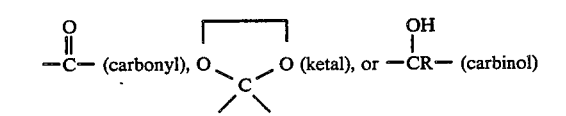

or a pharmaceutically acceptable acid addition salt and/or solvate thereof wherein X is $$\underset{\text{(carbonyl)}}{-\overset{O}{\overset{\|}{C}}-}, \quad \underset{\text{(ketal)}}{O\diagdown_C\diagup O}, \quad \text{or} \quad \underset{\text{(carbinol)}}{-\overset{OH}{\overset{|}{C}R}-}$$

with R being $C_{1-4}$ alkyl, hydrogen, or fluorophenyl; Y is halogen or hydrogen; and Z is alkoxy or hydrogen. There is a proviso that Y is only halogen when X is carbonyl and Z is hydrogen. As can be seen, Formula XXI encompasses both Formula I and Formula I' compounds. The preferred solvate forms of compounds of Formula XXI are hydrates, i.e. compounds complexed with water or hydration.

The compounds of I' are obtained according to the methods for I compounds previously set forth or by obvious modification of the procedures illustrated in Schemes 1 and 2 hereinabove. Preparation of the Formula I' compound (Id) wherein X is

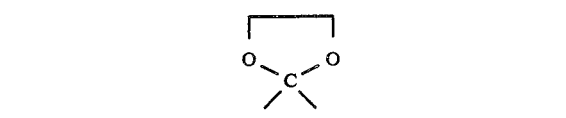

is shown below in Scheme 3. This compound is designated as Id for the sake of consistency in the numbering of related product compounds of the entire invention.

Scheme 3

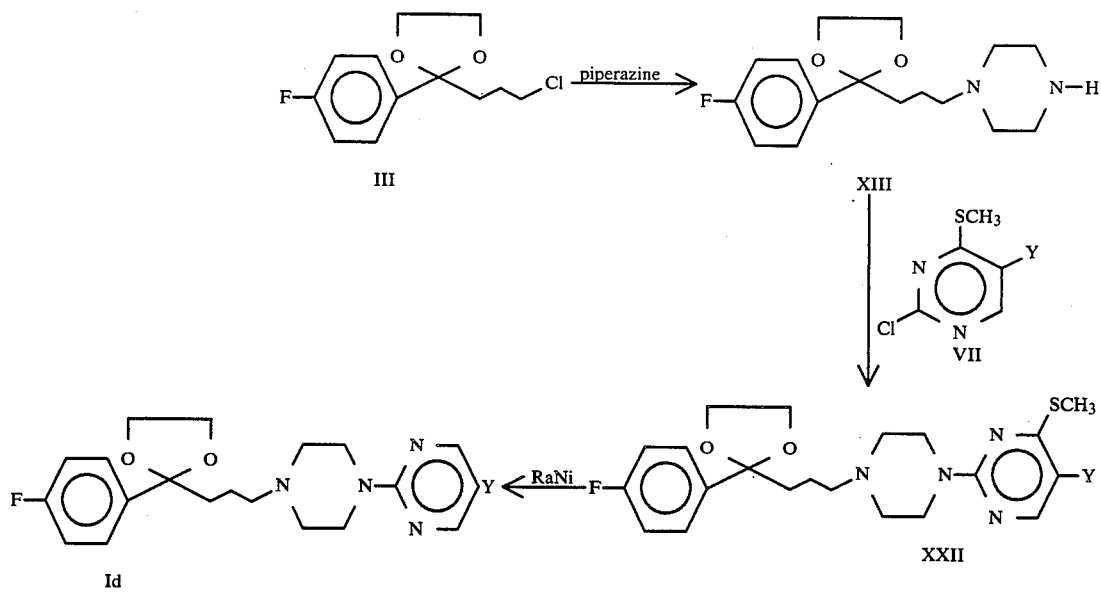

In this process the γ-chloro ketal (III; prepared from the commercially available ketone IV) is reacted with piperazine in the presence of potassium carbonate to give XIII which is then converted to XXII via an aromatic nucleophilic displacement reaction on the pyrimidine intermediate VII. Desulfurization by the standard Raney Nickel procedure affords the ketal structure of I'.

Compounds of Formula I' wherein Z is alkoxy may be prepared as shown in Scheme 4.

The procedure of Scheme 4 is mainly a modification of Scheme 1. Beginning with the ketal thiomethyl intermediate compound XXII, a selected alkoxy species is used to displace the methylthio moiety to give the desired (Z=OR) I'd product. This compound may be converted to any of the other desired I'a-c products wherein the structure of X is varied by using the reactions shown. In Schemes 3 and 4, as given above, R, X, Y, and Z are all as previously defined.

Preparation of any compound of Formula XXI may be achieved by means of the following unitary process.

Scheme 4

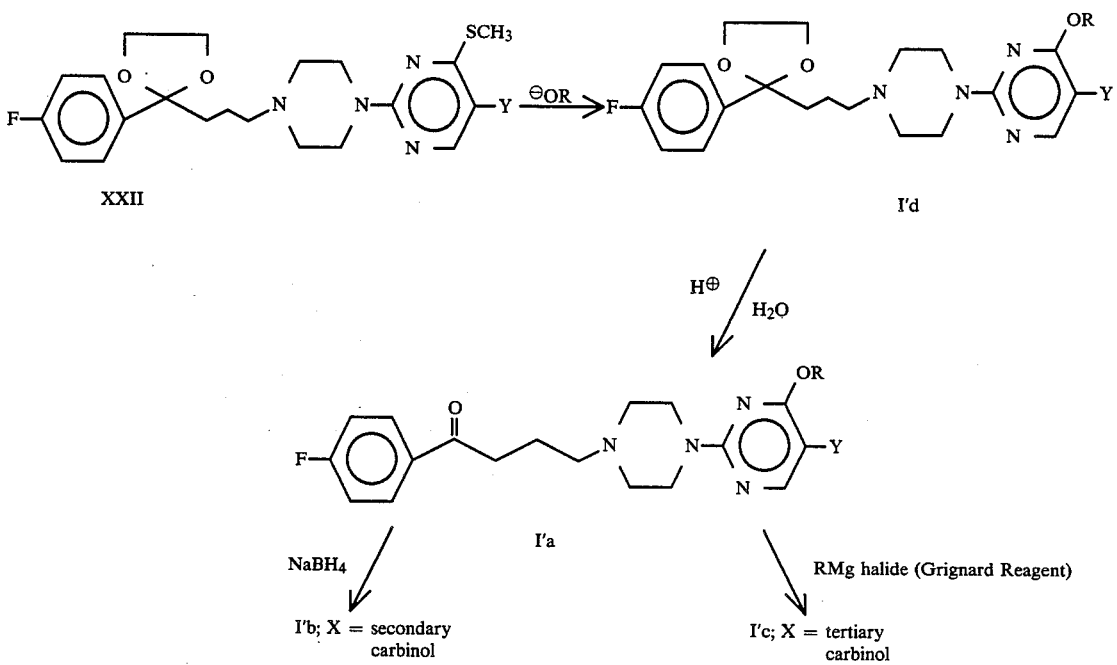

Synthesis of XXI Compounds
Unitary Process

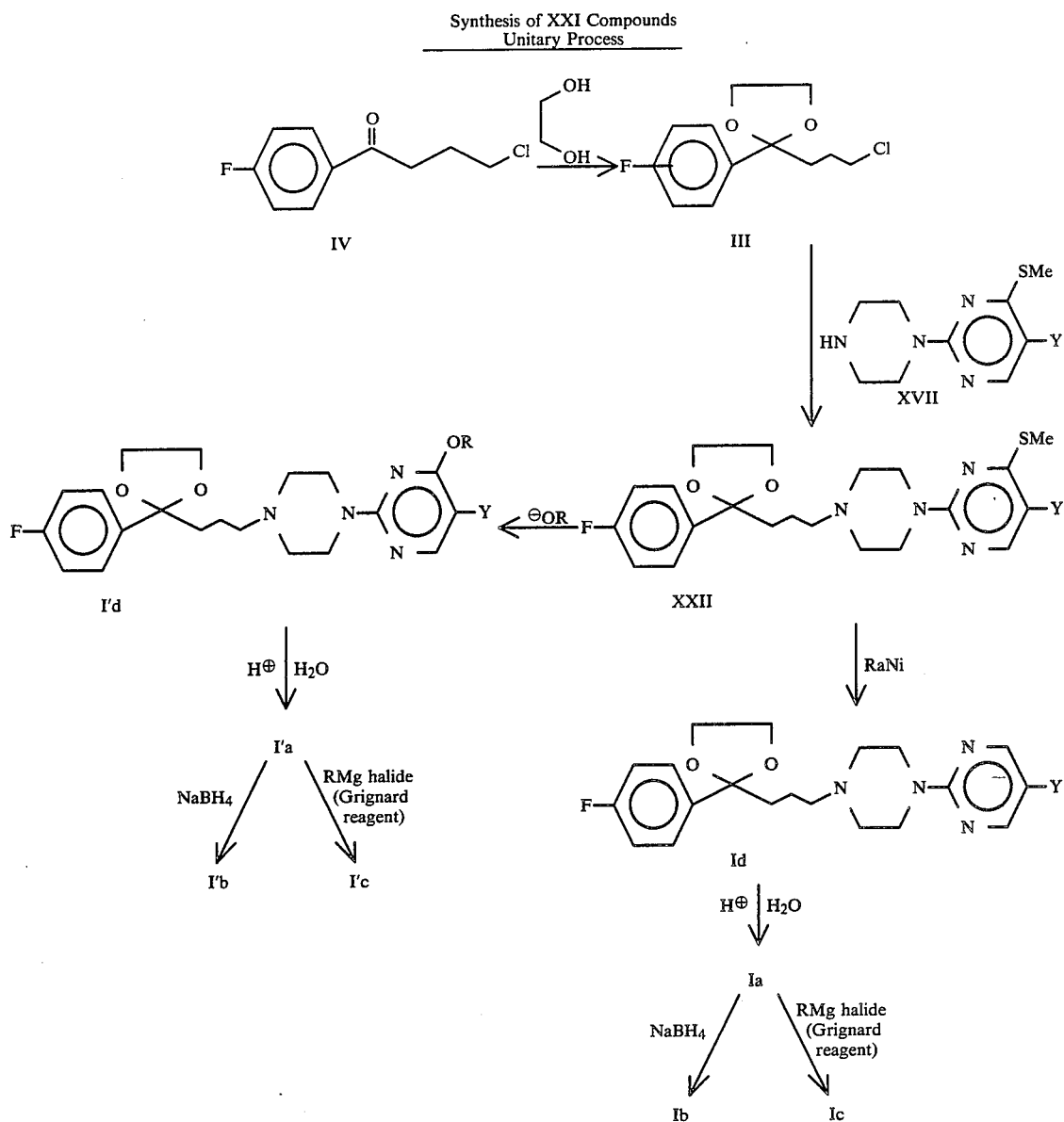

In the above scheme R and Y are as previously defined.

Another aspect of the invention concerns the stereoisomers of the preferred compound of Formula XXII. This compound which is also known as BMY 14802 and, as marked with an asterisk,

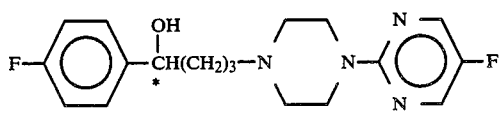

BMY 14802 possesses a chiral center and therefore exists as (−) and (+) enantiomers.

To resolve racemic BMY 14802 into its enantiomers, the racemic free base was treated with either S—(−)— or R—(+)—α-methylbenzyl isocyanate to afford mixtures of diastereomeric carbamates. The pure crystalline diastereomers obtained from reaction with the S—(−) and R—(+) isocyanates were cleaved with trichlorosilane to afford the (−) and (+) enantiomers of BMY 14802. These isocyanate resolving agents are commercially available and utilization of such reagents in the resolution of racemic alcohols and amines has been described in the literature. Resolution of the subject enantiomers was accomplished using the procedure outlined in Scheme 5.

Scheme 5

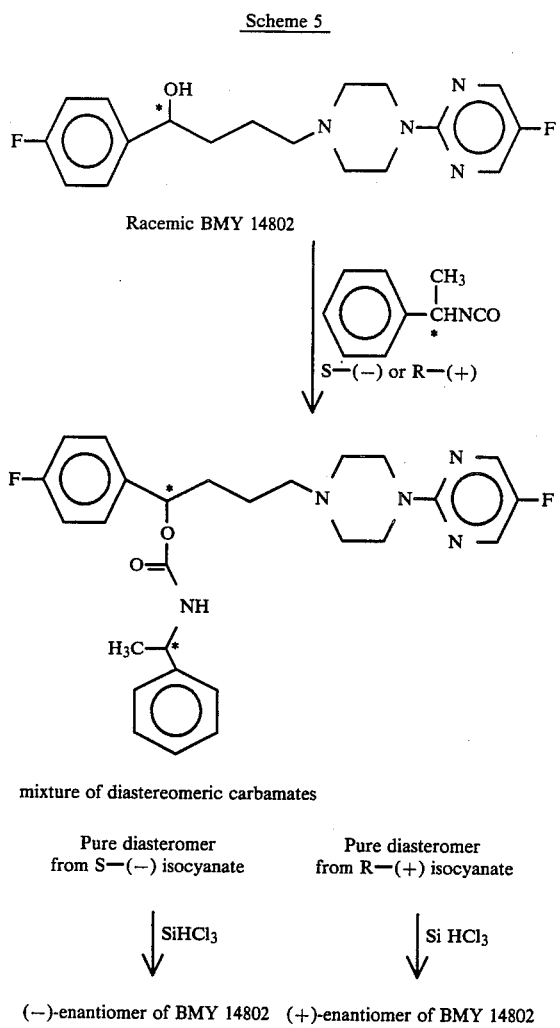

Ideally, two diasteromers should have been obtained from the reaction of racemic BMY 14802 regardless of isocyanate used. However, in each case one crystalline diastereomer was obtained by filtration and no further crystalline material could be obtained from the filtrate. Attempts to separate and isolate the second diastereomer from the filtrate using chromatography was unsuccessful. In practice, treatment of the racemic carbinol with the S—(—) isocyanate gave only one diastereomer in crystalline form which was isolated and cleaved with trichlorosilane to afford the pure (—)— enantiomer of BMY 14802. Similarly, the R—(+) isocyanate gave the pure crystalline diastereomer which could be cleaved to yield the (+)— enantiomer of BMY 14802.

Assessment of the biological activity of the enantiomers demonstrated that the (—)— enantiomer was more potent than racemic material in inhibiting apomorphine stereotypy in rats, but was less potent in the reversal of neuroleptic-induced catalepsy. The converse was true for the (+)— enantiomer of BMY 14802. This led to the conclusion that no significant advantage in pharmacological profile as a potential antipsychotic agent existed for either enantiomer compared to the racemic mixture.

EXAMPLE 19

5-Fluoro-2-[4-[3-[2-(4-fluorophenyl)-1,3-dioxolan-2-yl]-propyl]-1-piperazinyl]-pyrimidine Hydrochloride (I')

A mixture of the γ-chloro ketal (III; 27.49 g, 0.112 mole); piperazine (48.24 g, 0.56 mole); potassium carbonate (46.43 g, 0.33 mole); and a catalytic amount of potassium iodide, all in 358 mL of acetonitrile were refluxed for 18 hr. The hot reaction mixture was filtered and the filtrate concentrated in vacuo to a residue which was partitioned between water (250 mL) and ether. The water layer was extracted further with ether, the ether extracts combined and dried (MgSO$_4$) and concentrated in vacuo to give 28.5 g of 1-[3-[2-(4-fluorophenyl)-1,3-dioxolan-2-yl]piperazine (XIII).

The piperazine intermediate (XIII; 7.8 g, 0.026 mole); 2-chloro-5-fluoro-4-methylthio-2-pyrimidine (4.73 g, 0.026 mole); pulverized potassium carbonate (11.05 g); and a catalytic amount of potassium iodide in 80 mL acetonitrile was refluxed 18 hr. The hot reaction mixture was filtered and the filtrate was concentrated in vacuo to give 11.1 g of residue which was flash chromatographed (3% methanol/methylene chloride). Appropriate fractions were combined, dissolved in 10 mL ethanol, chilled and treated with ethanolic HCl from which 1.5 g of 5-fluoro-2-[4-[3-[2-(4-fluorophenyl)-1,3-dioxolan-2-yl]propyl]-1-piperazinyl]-4-(methylthio)-pyrimidine hydrochloride, (XXII) m.p. 233°–235° was obtained.

Anal. Calcd. for $C_{21}H_{26}F_2N_4O_2S \cdot HCl$: C, 53.33; H, 5.75; N, 11.85. Found: C, 53.53; H, 5.81; N, 12.03.

5-Fluoro-2-[4-[3-[2-(4-fluorophenyl)-1,3-dioxolan-2-yl]-propyl]-1-piperazinyl]-4-methylthio]pyrimidine (XXII; 7.45 g, 0.017 mole); triethylamine (3.05 g, 0.034 mole); 2 teaspoons of Raney Nickel in water were mixed in ethanol (125 mL) and refluxed 18 hr. The hot reaction mixture was filtered and the filtrate was concentrated in vacuo to about 1/5 volume. A crude crystalline product was obtained by filtration and its recrystallization in 20–25 mL ethanol gave 1.6 g of solid, m.p. 220°–222°. This solid was converted to the hydrochloride salt in ethanol using ethanolic HCl. Filtration and drying gave 1.6 g of product, m.p. 242°–244°.

Anal. Calcd. for $C_{20}H_{24}F_2N_4O_2 \cdot HCl$: C, 56.27; H, 5.90; N, 13.12. Found: C, 56.12; H, 6.06; N, 21.90.

EXAMPLE 20

4-(5-Fluoro-4-methoxy-2-pyrimidinyl)-δ-(4-fluorophenyl)-1-piperazinebutanol Hydrochloride Following the procedures given in Examples 6–8, but using 2-chloro-5-fluoro-4-methylthiopyrimidine as a starting material, the carbinol intermediate compound 4-[5-fluoro-4-(methylthio)-2-pyrimidinyl]-4-[4-fluorophenyl]-1-piperazinebutanol may be synthesized. A 3.77 g (0.01 mole) portion of this intermediate was combined with KOH (7.54 g) in methanol (75 mL) was refluxed for 18 hr. The methanol was removed in vacuo and the extract dissolved in water. The aqueous solution was extracted with ethyl ether, the ether extracts combined, dried, and concentrated in vacuo to 2.2 g of a residue which was flash chromatographed (ethyl acetate). The appropriate fractions were combined to give 1.6 g of oily product which was converted to the hydrochloride salt with ethanolic HCl to give 1.5 g of I'd product, m.p. 235°–237°.

Anal. Calcd. for $C_{19}H_{24}F_2N_4O_2 \cdot HCl$: C, 55.01; H, 6.07; N, 13.50. Found: C, 55.02; H, 6.22; N, 13.28.

EXAMPLE 21

Isolation of (−)-α-(4-Fluorophenyl)-4-(5-fluoro-2-pyrimidinyl)-1-piperazinebutanol Hydrate A mixture of α-(4-fluorophenyl)-4-(5-fluoro-2-pyrimidinyl)-1-piperazinebutanol (BMY 14802; 9.47 g. 0.027 mole) in 400 mL benzene was stirred and heated under reflux for 4 hr. with an attached Dean Stark trap for azeotropic removal of water of hydration. After cooling to room temperature, S—(−)-α-methylbenzyl isocyanate was added and the mixture stirred under $N_2$ for 18–20 hr. After staying at room temperature for 60 hr, the mixture was freed of solvent in vacuo and the residue flash-chromatographed on silica gel using ethyl acetate as eluant. Removal of solvent in vacuo afforded 13.07 g of an oil which was dissolved in 5–7 mL of ethanol and refrigerated. The resulting crystalline precipitate was collected by filtration and dried in vacuo at 70° to provide 5.13 g of carbamate derivative, m.p. 117°–119°. Proton NMR showed this material to be a single diasteromer.

The carbamate obtained above (4.75 g, 0.0096 mole) and triethylamine (1.17 g, 0.0116 mole) in 60 mL benzene was stired under an $N_2$ atmosphere. Trichlorosilane (1.44 g, 0.0106 mole) in 30 mL benzene was added dropwise over approximately 20 min. The mixture was stirred at room temperature for 20 hr and heated under reflux for 1 hr. The reaction mixture was extracted with $2 \times 100$ mL of saturated ammonium chloride solution. The aqueous extract was made basic with sodium carbonate and extracted with methylene chloride. After drying ($MgSO_4$), the methylene chloride extract was concentrated in vacuo and the residue flash chromatographed on silica gel using methylene chloride:methanol (19:1) as eluent. Fractions containing the component of Rf 0.44 (methylene chloride/methanol, 19:1) were combined and freed of solvent in vacuo to afford 2.04 g of solid which was recrystallized from ethanol to afford 1.3 g of the (−)-enantiomer of BMY 14802, m.p. 123°–125°, $[\alpha]_D^{25} = -15.2°$ (concentration of 0.5% by weight in methanol). The yield of the (−)-enantiomer based on racemic material was 27.3%.

Anal. Calcd. for $C_{18}H_{22}F_2N_4O \cdot 0.25H_2O$ (MW=352.9): C, 61.26; H, 6.43; N, 15.88; $H_2O$, 1.28. Found: C, 61.29; H, 6.46; N, 15.85; $H_2O$, 1.33.

EXAMPLE 22

Isolation of (+)—α-(4-Fluorophenyl)-4-(5-fluoro-2-pyrimidinyl)-1-piperazinebutanol Hydrate The procedure followed was identical to that described in Example 21 above. From racemic BMY 14802 free base (9.47 g, 0.027 mole) and R—(+)—α-methylbenzyl isocyanate (4.0 g, 0.027 mole) in 400 mL benzene was obtained after chromatography and recrystallization 5.3 g of carbamate, m.p. 117°–119°. Proton NMR confirmed this material to be a single diasteromer.

Continuing with the procedure of Example 21 above, the carbamate (5.29 g, 0.0107 mole) was treated with trichlorosilane (1.59 g, 0.0117 mole) in the presence of triethylamine (1.29 g, 0.0127 mole) in benzene (90 mL). Following chromatography and recrystallization, there was obtained 2.2 g, of the (+)-enantiomer of BMY 14802, m.p. 123°–125°, $[\alpha]_D^{25} = +15.4°$ (concentration of 0.5% by weight in methanol). The yield based on racemic material was 44.5%.

Anal. Calcd. for $C_{18}H_{22}F_2N_4O \cdot 0.25H_2O$ (MW=352.9): C, 61.26; H, 6.43; N, 15.88; $H_2O$, 1.28. Found: C, 61.27; H, 6.50; N, 16.14; $H_2O$, 1.31.

What is claimed is:

1. A compound of Formula XXI

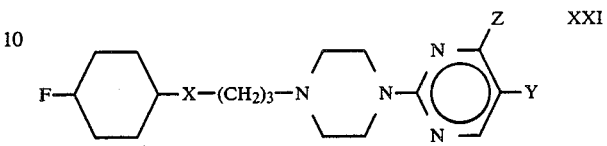

and its pharmaceutically acceptable acid addition salts and/or hydrates thereof, wherein X is

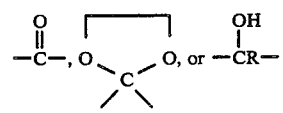

with R being $C_{1-4}$ alkyl, hydrogen, or fluorophenyl,

Y is halogen; and

Z is lower alkoxy or hydrogen.

2. A compound of claim 1 wherein X is

and Y is halogen.

3. The compound of claim 2, 1-(4-fluorophenyl)-4-[4-(5-fluoro-2-pyrimidinyl)-1-piperazinyl]butanone hydrochloride.

4. The compound of claim 1 wherein X equals

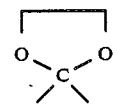

and Y is halogen.

5. The compound of claim 4, 5-fluoro-2-[4-[3-[2-(4-fluorophenyl)-1,3-dioxolan-2-yl]propyl]-1-piperazinyl]-pyrimidine hydrochloride.

6. The compound of claim 1 wherein X is —CHOH— and Y is halogen.

7. The compound of claim 6, 4-(5-bromo-2-pyrimidinyl)-α-(4-fluorophenyl)-1-piperazinebutanol hydrochloride.

8. The compound of claim 6, 4-(5-chloro-2-pyrimidinyl)-α-(4-fluorophenyl)-1-piperazinebutanol hydrochloride.

9. The compound of claim 6, 4-(5-fluoro-4-methoxy-2-pyrimidinyl)-δ-(4-fluorophenyl)-1-piperazinebutanol hydrochloride.

10. The compound of claim 1 wherein Y equals fluoro.

11. The compound of claim 6 wherein Y equals fluoro.

12. The compound of claim 11, 4-[4-[5-fluoro-2-pyrimidinyl]-1-piperazinyl]-1-(4-fluorophenyl)butanol.

13. The compound of claim 11, 4-[4-[5-fluoro-2-pyrimidinyl]-1-piperazinyl]-1-(4-fluorophenyl)butanol hydrochloride.

14. The compound of claim 12, (−)-α-(4-fluorophenyl)-4-(5-fluoro-2-pyrimidinyl)-1-piperazinebutanol hydrate.

15. The compound of claim 11, (+)-α-(4-fluorophenyl)-4-(5-fluoro-2-pyrimidinyl)-1-piperazinebutanol hydrate.

16. The method for ameliorating an undesirable psychotic state in a mammal comprising oral administration to said mammal of an effective antipsychotic amount of a compound claimed in claim 1.

17. The method of claim 16 wherein the formula I compound is 4-[4-[5-fluoro-2-pyrimidinyl]-1-piperazinyl]-1-(4-fluorophenyl)butanol or a pharmaceutically acceptable acid addition salt thereof.

18. The method for ameliorating an undesirable psychotic state in a mammal comprising parenteral administration to said mammal of an effective antipsychotic amount of a compound claimed in claim 1.

19. The method of claim 18 wherein the Formula I compound is 4-[4-[5-fluoro-2-pyrimidinyl]-1-piperazinyl]-1-(4-fluorophenyl)-butanol or a pharmaceutically acceptable acid addition salt thereof.

20. A pharmaceutical composition in dosage unit form suitable for systemic administration to a mammalian host comprising a pharmaceutical carrier and from about 1 to 500 mg of a compound claimed in claim 1.

21. The pharmaceutical composition of claim 20 wherein the Formula I compound is 4-[4-[5-fluoro-2-pyrimidinyl]-1-piperazinyl]-1-(4-fluorophenyl)butanol or a pharmaceutically acceptable acid addition salt thereof.

* * * * *